US009867958B2

United States Patent
McCaslin

(10) Patent No.: US 9,867,958 B2
(45) Date of Patent: Jan. 16, 2018

(54) AUTO-ADJUSTING MEMBRANE FOR RESPIRATORY INTERFACE DEVICE

(71) Applicant: KONINKLIJKE PHILIPS N.V., Eindhoven (NL)

(72) Inventor: Jonathan Paul McCaslin, Renfrew, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 537 days.

(21) Appl. No.: 14/394,828

(22) PCT Filed: Apr. 12, 2013

(86) PCT No.: PCT/IB2013/052911
§ 371 (c)(1),
(2) Date: Oct. 16, 2014

(87) PCT Pub. No.: WO2013/156910
PCT Pub. Date: Oct. 24, 2013

(65) Prior Publication Data
US 2015/0047640 A1 Feb. 19, 2015

Related U.S. Application Data

(60) Provisional application No. 61/636,206, filed on Apr. 20, 2012.

(51) Int. Cl.
*A61M 16/06* (2006.01)
*A61M 16/08* (2006.01)

(52) U.S. Cl.
CPC .......... *A61M 16/065* (2014.02); *A61M 16/06* (2013.01); *A61M 16/0605* (2014.02);
(Continued)

(58) Field of Classification Search
CPC .............. A61M 16/06; A61M 16/0605; A61M 16/0611; A61M 16/0616; A61M 16/0622;
(Continued)

(56) References Cited

U.S. PATENT DOCUMENTS 5,074,297 A * 12/1991 Venegas ................ A61M 16/06
128/204.18
6,584,977 B1 7/2003 Serowski
(Continued)

FOREIGN PATENT DOCUMENTS

WO WO2012020359 A1 2/2012

OTHER PUBLICATIONS

"Measuring Silicone Rubber's Durometer"; retrieved from http://www.rubbercal.com/sheet-rubber/silicone-durometer.*

*Primary Examiner* — (Jackie) Tan-Uyen T Ho
*Assistant Examiner* — Joseph D Boecker
(74) *Attorney, Agent, or Firm* — Michael W. Haas

(57) ABSTRACT

A respiratory interface device is provided. The respiratory interface device includes a mask (10) having a faceplate (12) and a patient contacting cushion (15), the patient contacting cushion coupled to, and extending about, the faceplate, a brace assembly (40) having a brace body (42) with at least one mask coupling, the mask and the brace assembly coupled at the mask coupling, wherein the mask coupling is a soft coupling. The mask soft coupling utilizes a flexible membrane assembly, the flexible membrane assembly being disposed between the mask and the brace body.

9 Claims, 7 Drawing Sheets

(52) U.S. Cl.
CPC .... *A61M 16/0622* (2014.02); *A61M 16/0683* (2013.01); *A61M 16/0816* (2013.01); *A61M 16/0616* (2014.02); *A61M 16/0633* (2014.02); *A61M 2205/0216* (2013.01)

(58) Field of Classification Search
CPC .......... A61M 16/0633; A61M 16/0638; A61M 16/065; A61M 16/0666; A61M 16/0683; A61M 16/0816; A61M 16/0825; A62B 18/02; A62B 18/025; A62B 18/04; A62B 18/08
USPC .................. 128/205.25, 206.21, 206.24, 128/206.26–206.28, 207.11, 207.13
See application file for complete search history.

(56) References Cited

U.S. PATENT DOCUMENTS

| | | | |
|---|---|---|---|
| 6,763,835 B1 | 7/2004 | Grove | |
| 7,219,669 B1* | 5/2007 | Lovell | A61M 16/06 |
| | | | 128/205.25 |
| 2006/0042629 A1 | 3/2006 | Geist | |
| 2006/0201514 A1* | 9/2006 | Jones | A61M 16/06 |
| | | | 128/206.21 |
| 2006/0207599 A1 | 9/2006 | Busch | |
| 2006/0283456 A1 | 12/2006 | Geiselhart | |
| 2007/0044804 A1 | 3/2007 | Matula, Jr. | |
| 2007/0125385 A1 | 6/2007 | Ho | |
| 2008/0006270 A1* | 1/2008 | Gershman | A61M 16/0057 |
| | | | 128/203.28 |
| 2008/0066745 A1* | 3/2008 | Janbakhsh | A61M 16/06 |
| | | | 128/200.24 |
| 2009/0223521 A1* | 9/2009 | Howard | A61M 16/06 |
| | | | 128/206.23 |
| 2009/0223523 A1* | 9/2009 | Chang | A62B 18/08 |
| | | | 128/207.11 |
| 2010/0282264 A1* | 11/2010 | Chang | A61M 16/06 |
| | | | 128/206.21 |
| 2010/0319700 A1* | 12/2010 | Ng | A61M 16/06 |
| | | | 128/206.28 |
| 2011/0048425 A1* | 3/2011 | Chang | A61M 16/06 |
| | | | 128/206.24 |
| 2011/0232647 A1 | 9/2011 | Ho | |
| 2011/0277770 A1* | 11/2011 | Chang | A61M 16/0683 |
| | | | 128/206.21 |
| 2012/0080035 A1* | 4/2012 | Guney | A61M 16/06 |
| | | | 128/205.25 |
| 2012/0138061 A1* | 6/2012 | Dravitzki | A61M 16/06 |
| | | | 128/205.25 |
| 2014/0174446 A1* | 6/2014 | Prentice | A61M 16/06 |
| | | | 128/205.25 |

* cited by examiner

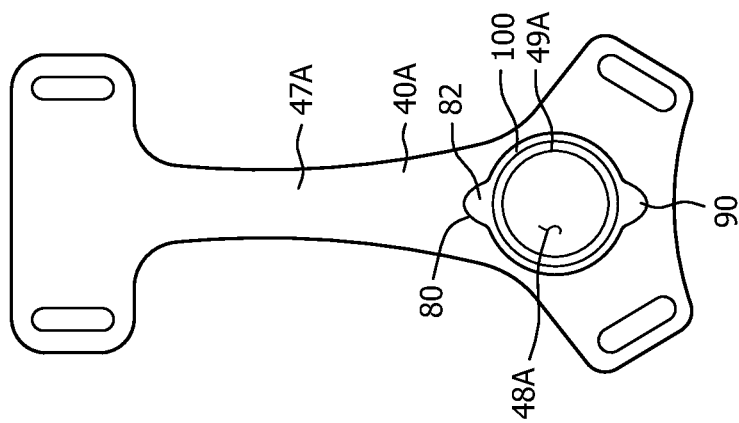
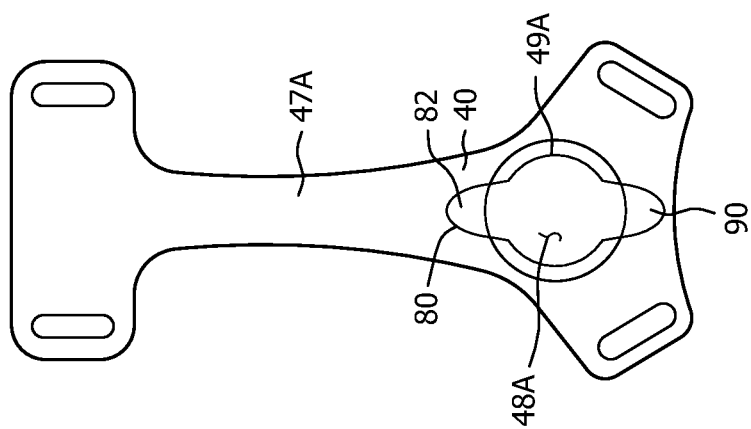
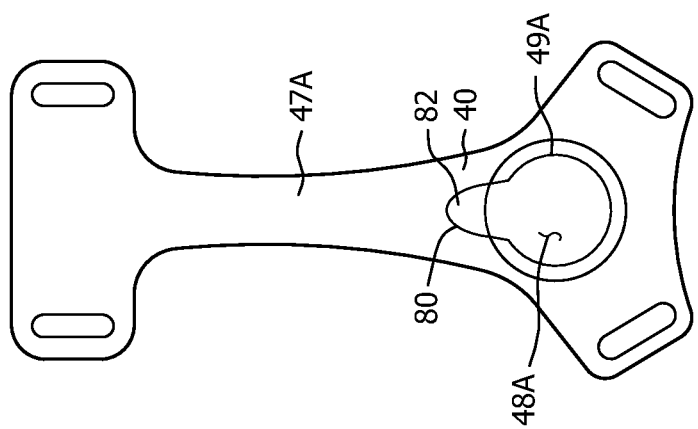

AUTO-ADJUSTING MEMBRANE FOR RESPIRATORY INTERFACE DEVICE

CROSS-REFERENCE TO RELATED APPLICATIONS

This patent application claims the priority benefit under 35 U.S.C. §371 of international patent application no. PCT/IB2013/052911, filed Apr. 12, 2012, which claims the priority benefit under 35 U.S.C. §119(e) of U.S. Provisional Application No. 61/636,206 filed on Apr. 20, 2012, the contents of which are herein incorporated by reference.

BACKGROUND OF THE INVENTION

1. Field of the Invention

The present invention relates to respiratory interface devices for transporting a gas to and/or from an airway of a user which include, but not limited to, a mask having a flexible faceplate or patient contacting cushion, and in particular to a flexible respiratory interface device that is supported by a brace and having a flexible membrane assembly disposed between the mask and the brace body.

2. Description of the Related Art

A variety of respiratory masks are known which cover the areas surrounding the nose and/or mouth of a human user and that are designed to create an effective fit against the user's face. Typically, gases can be provided at a positive pressure within the mask for consumption by the user. The uses for such masks include high altitude breathing (aviation applications), swimming, mining, fire-fighting, and various medical diagnostic and therapeutic applications.

One requisite of many of these masks, particularly medical respiratory masks, is that they provide an effective fit against the user's face and that the mask contours with the user's face to limit or prevent leakage of the gas being supplied. A common type of mask incorporates a single-piece faceplate or a two-piece faceplate, having an upper portion (e.g., to cover the nasal portion of a human user's face) and lower portion (e.g., to cover the mouth portion of a human user's face) that are unitary or coupled together by a flexible member. See, for example, U.S. Patent Pub. 2011/0232647 which is incorporated by reference.

The respiratory masks that are known also have a sealing surface or cushion around the periphery of the mask to seal against the user's face. The cushion is typically attached to the faceplate. Such masks have performed well when the fit is good between the contours of the seal surface and the corresponding contours of the user's face. This may occur, for example, if the mask is properly oriented and provides a good fit against the user's face and the mask contours with the user's face. If the mask is not properly oriented or if the fit is not good, there will be gaps in the mask-to-face interface resulting in gas leaking from the mask at the gaps. Considerable force will be required to compress the mask member to close the gaps and attain a satisfactory seal in those areas where the gaps occur.

Typically, this required force will be provided by straps that are connected to the mask or to a brace assembly to which the mask is coupled. Such force is undesirable because it produces high pressure points elsewhere on the face of the user where the mask contour is forcibly deformed against the face to conform to the user's facial contours. This will produce considerable user discomfort and possible skin irritation and breakdown anywhere the applied force exceeds the local perfusion pressure, which is the pressure that is sufficient to cut off surface blood flow.

For example, it is not uncommon to have a gap between the cushion and the user's face at the bridge of the nose or adjacent the bridge of the nose. When such a gap occurs, the user may adjust the straps by tightening or loosening the straps, as discussed above, or by moving the position of the straps relative to the user's face. Typically, the user would move the straps to a higher position on their face. This adjustment, however, places the straps closer to the user's eyes, which is generally considered to be uncomfortable. Alternatively, the respiratory interface device may be provided with additional straps so as to allow for better positioning of the respiratory interface device relative to the user's face. Additional straps, however, are also generally considered to be uncomfortable.

When a respiratory mask utilizes a brace assembly, the brace assembly is, typically, directly coupled to the mask in a fixed orientation. In this configuration, the bias created by the straps passes through the coupling between the brace assembly and the mask. Thus, the orientation of the mask relative to the user's face is affected by the bias on the brace assembly. For example, assuming there are two upper straps and two lower straps, if the user tightens the upper straps there will be a greater bias on the upper portion of the brace assembly and therefore the upper portion of the mask will be more biased toward the user's face. That is, the mask will not be properly oriented in that the mask is, essentially, tilted upwardly. This may create a gap along the lower edge of the mask sealing surface. The user must then tighten the lower straps to compensate. The user, however, may overcompensate thereby creating a gap along the upper edge of the mask sealing surface. Such strap adjustments may continue and may result in a mask that is too tight or otherwise uncomfortable.

Accordingly, a need exists to provide a respiratory interface device capable of providing a more complete seal between the patient's face and the cushion without having to adjust the straps and/or adjust the straps in a manner that is uncomfortable for the user. Further, a need exists to provide a respiratory interface device capable of automatically orienting the mask in a proper orientation.

SUMMARY OF THE INVENTION

One embodiment of the present invention provides a respiratory interface device including a mask and a brace assembly. The mask has a faceplate and a patient contacting cushion. The patient contacting cushion is coupled to, and extends about, the faceplate. The brace assembly includes a rigid brace body to which straps may be attached. The mask is movably coupled to the brace body. That is, the mask may rotate relative to at least one axis, e.g. a horizontal axis, or in an exemplary embodiment the mask may pivot relative to at least two axes, a horizontal axis and a vertical axis.

A flexible membrane assembly is disposed between the mask and the brace body. The flexible membrane assembly includes at least a first elongated member extending between the mask and the brace body. The first elongated member is resilient and deformable, but not overly deformable. Thus, when the straps are tightened about the user's head, the brace body is biased toward the mask. The brace body engages the first elongated member that may be compressed, or otherwise deformed slightly. Thus, the first elongated member absorbs some of the force created by the adjustment of the brace body being biased toward the user's face. Moreover, the flexible membrane assembly is structured to automatically adapt to different facial geometries and properly orient the mask relative to the user's face. That is, unlike a rigid coupling between the mask and the brace assembly, as in the prior art, the flexible membrane assembly provides a soft coupling between the mask and the brace assembly wherein the mask is movably coupled to the brace assembly.

For example, the flexible membrane assembly may include a torus shaped flexible membrane extending about a gas source coupling device, typically a circular tube providing gas to the mask and user. For users having a less pronounced nasal root, and when the mask is placed over the user's face and the straps on the brace assembly are tightened, the upper portion of the membrane will only be slightly compressed, or not compressed at all, causing the mask to rotate slightly about a horizontal axes relative to the brace body. Thus, the mask is automatically placed in a proper orientation. For users with a more pronounced nasal root, and when the mask is placed over the user's face and the straps on the brace assembly are tightened, the dorsum of the nose engaging the mask will cause the mask to rotate relative to the brace assembly. As the mask, as well as the membrane, rotates the membrane engages the brace assembly and causes the upper portion of the membrane to be compressed to a greater degree than with a user with a flat nose. The compressed membrane maintains the mask in the proper orientation. With the proper orientation, and with the bias created by the tightened straps, the mask has a more complete seal than a device with fixed couplings between the mask and brace assembly. Further, the position of the mask relative to the brace body is automatically adjusted to the user's facial contour.

It is an object of this invention to provide a respiratory interface device including a mask having a faceplate and a patient contacting cushion, the patient contacting cushion coupled to, and extending about, the faceplate, a brace assembly having a brace body with at least one mask coupling, the mask and the brace assembly coupled at the mask coupling, wherein the mask coupling is a soft coupling. It is a further object of this invention to provide a mask soft coupling that utilizes a flexible membrane assembly, the flexible membrane assembly being disposed between the mask and the brace body.

It is an object of this invention to provide a method of utilizing a respiratory interface device having a soft coupling between the mask and the brace assembly, the soft coupling having a flexible membrane assembly, including the steps of positioning the mask over the patient's nose and mouth thereby creating a generally continuous seal between the patient's face and the cushion, compressing at least a portion of the flexible membrane assembly thereby allowing selective, but limited, movement of the mask relative to the brace assembly, and creating a more complete seal between the patient's face and the cushion.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 5 is a front view of a brace assembly with one embodiment of a flexible membrane assembly;

FIG. 6 is a front view of a brace assembly with another embodiment of a flexible membrane assembly;

FIG. 7 is a front view of a brace assembly with a another embodiment of a flexible membrane assembly;

DETAILED DESCRIPTION OF EXEMPLARY EMBODIMENTS

Figure 1:
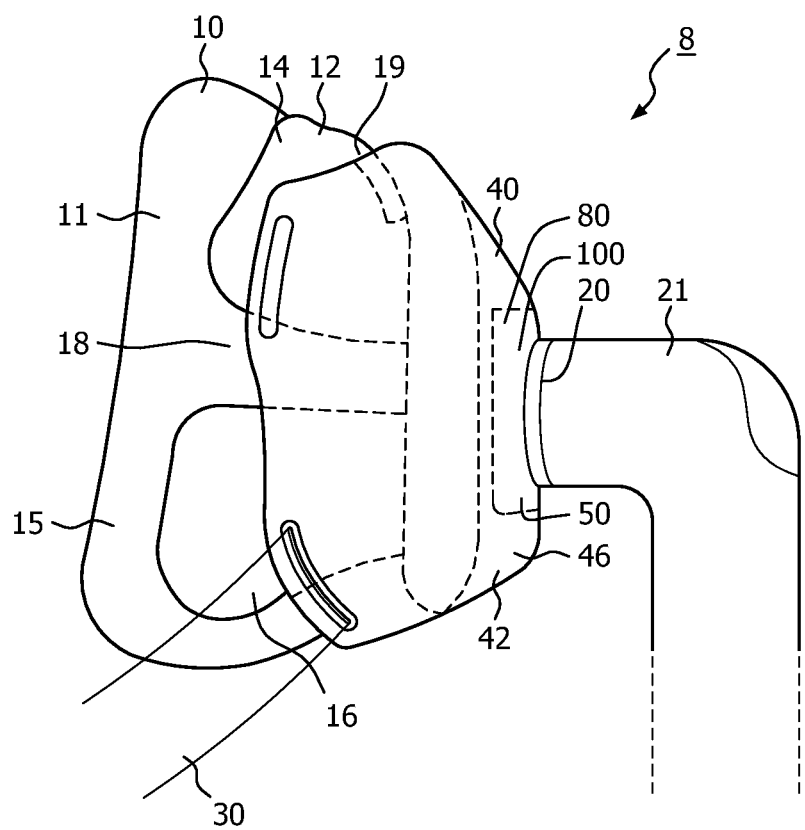
FIG. 1 is a side view of an exemplary embodiment of a respiratory mask.

As used herein, the singular form of "a", "an", and "the" include plural references unless the context clearly dictates otherwise. As used herein, the statement that two or more parts or components are "coupled shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, a "contact coupling" means that contacting parts are biased toward each other. That is, parts that merely contact each other without any bias do not form a "contact coupling."

As used herein, "rigid" means inflexible and non-compressible. As used herein, "stiff" means substantially inflexible and non-compressible but allowing for minimal bending or compression. As used herein, "soft" means allowing for bending or compression while maintaining some resiliency; for example a typical balloon is "soft."

As used herein, a "soft coupling" is a coupling structured to maintain two spaced components in a substantially constant orientation relative to each other; for example, two components generally held in a spaced relation by either stiff or soft fasteners, or, two components generally held in a spaced relation by a coupling with either a stiff or soft member disposed between the components.

As used herein, a "soft direct coupling" is a type of "soft coupling" structured to maintain two spaced components in a substantially constant orientation relative to each other and wherein a portion of at least one of the components extends toward the other and directly contacts the other component.

As used herein, a "floating coupling" or is a coupling wherein a portion of a first component is trapped within a portion of, but not fixed to, another, second component. That is, a portion of the second component defines an opening and the portion of the first component extends therethrough and cannot escape. For example, a first chain link is floatably coupled to a second chain link. That is, a portion of the first link passes through and is trapped within the loop, or opening, formed by the second chain link; the first link, however, is not fixed to the second link and, other than being separated therefrom, may move relative thereto.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall means that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein. Further, as used herein, "inwardly" means in a direction toward the user's face and "outwardly" means in a direction away from the user's face.

As used herein, when discussing an element moving between two positions, e.g. a rod moving between a first position and a second position, "between" means at the first or at the second position, as well as any position therebetween.

As used herein, a "coupling" is one element of a coupling assembly. That is, a coupling assembly includes at least two elements, or couplings, that are structured to be coupled together. It is understood that the elements of a coupling assembly correspond to each other. For example, in a coupling assembly, if one coupling element is a bolt, the other coupling element is a nut. As a further example, in a coupling assembly, if one coupling element is a snap socket, the other coupling element is a snap plug. Further, it is understood that the two elements of a coupling assembly may not be described at the same time.

As used herein, the "bridge" of the nose is the area of the nose between the eyes. As used herein, the "dorsum" of the nose is the elongated area of the nose below the bridge and above the tip. The "dorsum" is, typically, aligned with the centerline of the face. The sides of the nose are not part of the dorsum. As used herein, "aligned" means "on the same line as" or "parallel to." As used herein, "a generally continuous seal" may have a gap or may gap when the user moves.

As used herein, "a more complete seal" has a gap that is shorter in length than a gap of a generally continuous seal, or, is resistant to gapping when the user moves.

Figure 2:
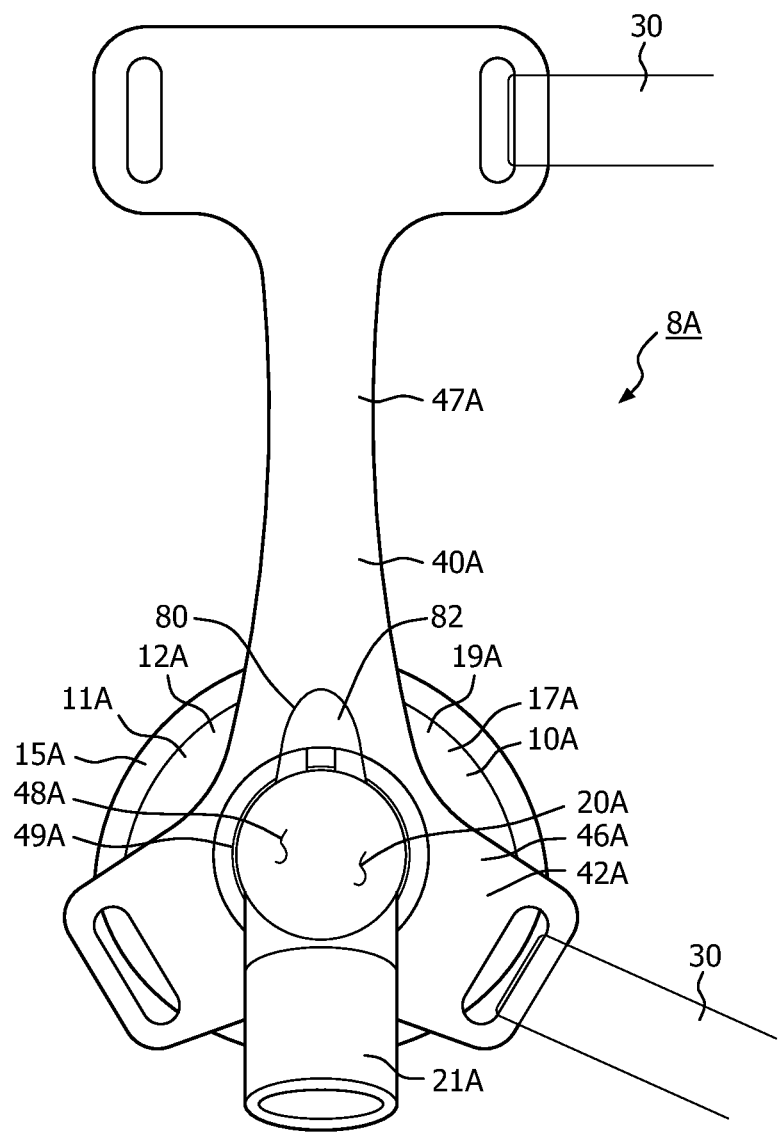
FIG. 2 is a front view of another exemplary embodiment of a respiratory mask.

Two exemplary embodiments of respiratory masks 10, 10A are shown in FIGS. 1 and 2, respectively. It is understood that the first exemplary embodiment is a larger mask 10 structured to cover the nose and mouth of the user. Further, the elements of this exemplary embodiment are identified by reference numbers without any letter. It is understood that the second exemplary embodiment is a smaller mask 10A structured to cover the nose of the user. Further, the elements of this exemplary embodiment are identified by reference numbers followed by the letter "A". Finally, it is understood that reference to mask 10 will refer only to FIG. 1 and that reference to the second exemplary embodiment may referred to any of FIGS. 2-8.

Respiratory interface device 8, 8A includes a respiratory mask 10, or 10A, and a brace assembly 40, 40A. Mask 10, 10A is coupled to a pressure generating system (not shown) via a patient circuit, as is conventionally known in the art. For purposes of the present invention, the pressure generating system is any device capable of generating a flow of breathing gas or providing gas at an elevated pressure. Examples of such pressure generating systems include a ventilator, CPAP device, or variable pressure device, e.g. an auto-titrating device, proportional assist ventilation (PAV) device, proportional positive airway pressure (PPAP) device, C-Flex™. device, Bi-Flex™. device, or a BiPAP™. device manufactured and distributed by Philips Respironics of Murrysville, Pa., in which the pressure provided to the patient varies with the patient's respiratory cycle so that a higher pressure is delivered during inspiration than during expiration, or other pressure support device.

Mask 10, 10A includes a body 11, 11A with a faceplate 12, 12A and a cushion 15, 15A, discussed below. In an exemplary embodiment, faceplate 12, 12A is substantially rigid. Faceplate 12, 12A has an outer side 19, 19A. In an exemplary embodiment (not shown) faceplate 12 may be a single piece structured to cover the user's nose and mouth. In such an embodiment, body 11 is coextensive with faceplate 12. In another exemplary embodiment, shown in FIG. 1, faceplate 12 has upper portion 14 and lower portion 16. In this embodiment, body 11 further includes a substantially flexible connecting member 18 that extends between upper and lower portions 14 and 16, respectively. Connecting member 18 is structured to at least partially connect upper portion 14 to lower portion 16. Specifically, a first side of connecting member 18 is coupled to upper portion 14 and a second, opposite side, is coupled to lower portion 16. Upper and lower portions 14, 16 are typically, although not necessarily, generally rigid. That is, faceplate upper portion 14 may also be identified as a "first substantially rigid portion" and faceplate lower portion 16 may be identified as a "second substantially rigid portion."

Connecting member 18 is a flexible, resilient member. In an exemplary embodiment of the present invention, connecting member 18 is made of, for example, a thermoplastic or thermoelastic material, including but not limited to an elastomer such as plastic, rubber, silicone, vinyl, foam, or any combination thereof. It is contemplated in the present invention that connecting member 18 can be formed in various shapes and geometries. In one embodiment, connecting member 18 provides a groove between upper and lower portions 14, 16. The groove (as shown in FIG. 1) can be structured to form a concave shape (e.g., an inward barrel shape). Alternatively, the groove can form a convex shape (e.g., an outward barrel shape). Connecting member 18 is structured to be flexible such that it can move in a hinge-like manner. Such hinge-like movement allows upper portion 14 to flex or move independently or separately from and relative to lower portion 16. Thus, mask 10 can provide improved contouring to the user's face, and therefore result in an effective fit. The particular connecting member 18 shown in FIG. 2 is not meant to be limiting and it should be understood that the present invention contemplates a variety of different configurations for flexible connecting member 18. Thus, various flexible connecting members may be substituted for connecting member 18.

Figure 3:
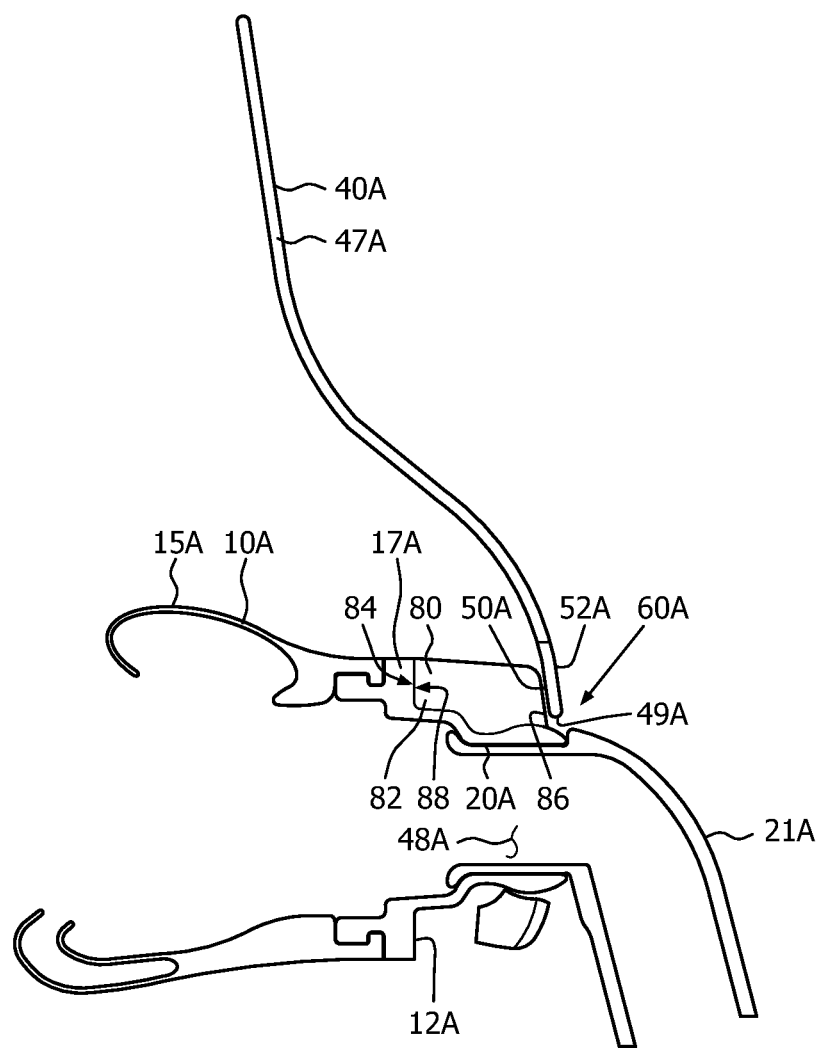
FIG. 3 is a cross-sectional side view of the exemplary embodiment of a respiratory mask shown in FIG. 2.
Figure 4:
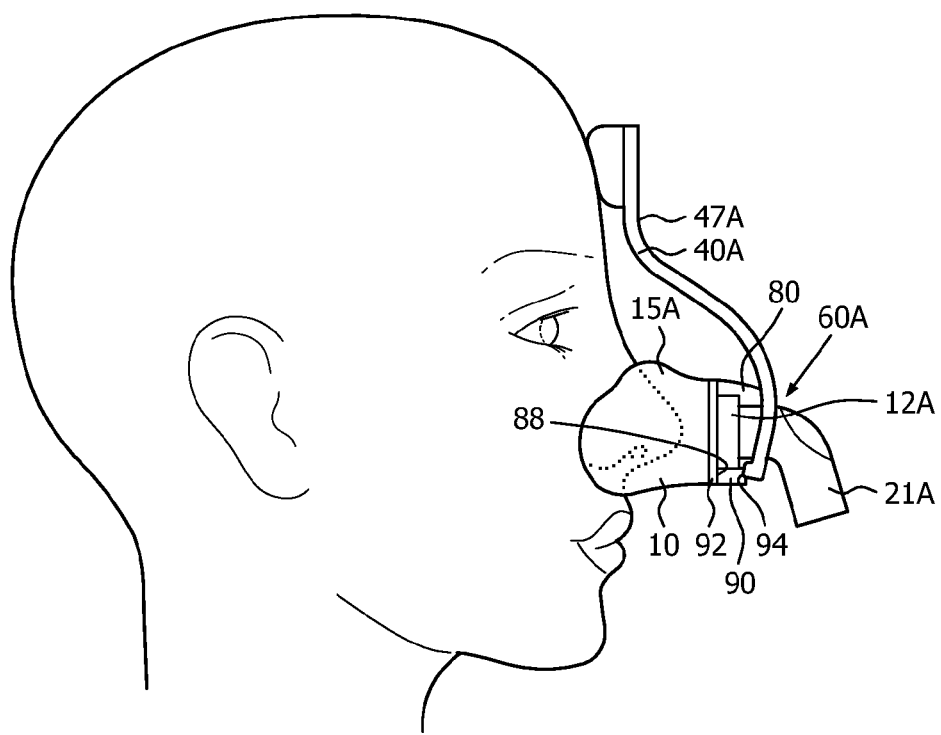
FIG. 4 is a side view of the exemplary embodiment of a respiratory mask shown in FIG. 2.
Figure 8:
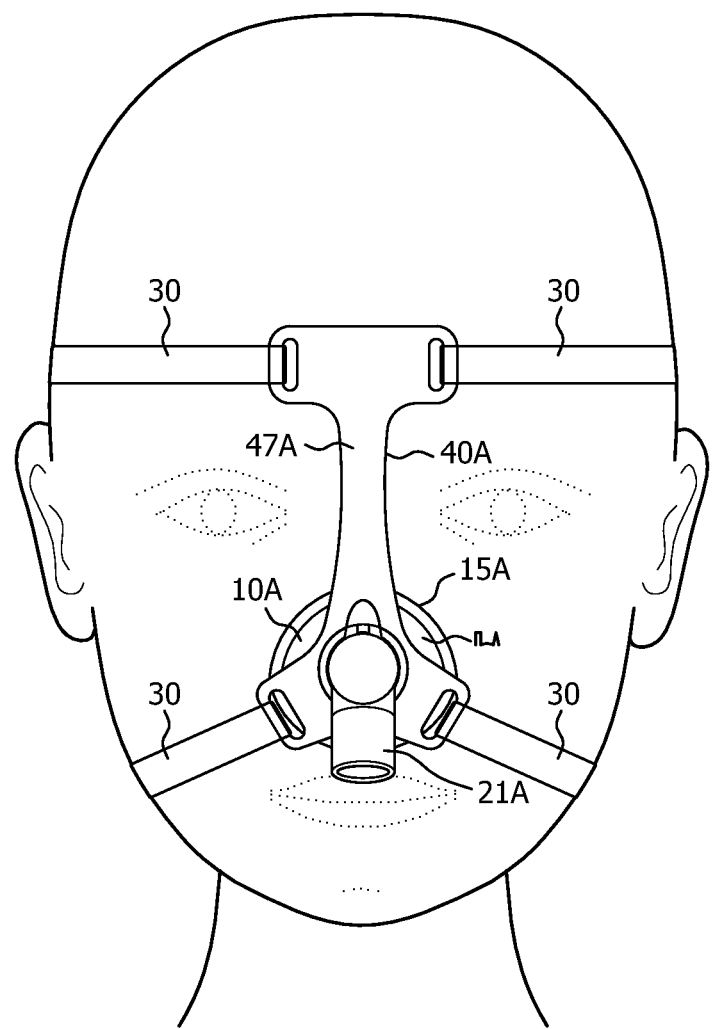
FIG. 8 is a front view of another exemplary embodiment of a respiratory mask on a user.
Figure 9:
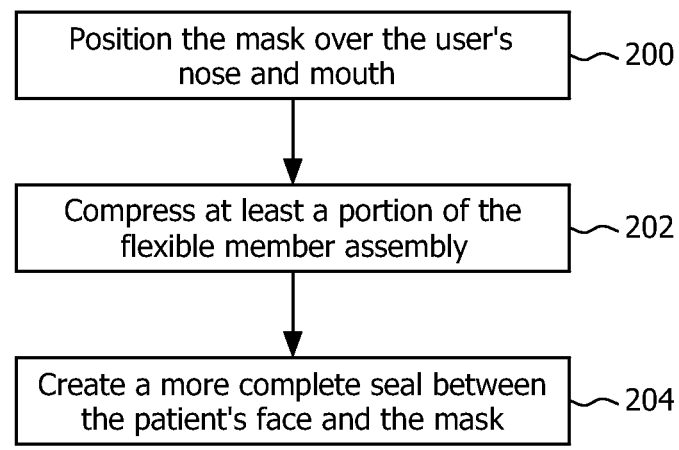
FIG. 9 is a flowchart of the step associated with using any exemplary embodiment of a respiratory mask.

In an exemplary embodiment, shown in FIGS. 2-4, faceplate 12A is a single piece structured to cover the user's nose only. In the exemplary embodiment shown in FIGS. 2-4, faceplate 12A is a generally cylindrical, rigid body 17A. Faceplate 12A has an outer side 19A. Faceplate 12A defines an opening 20A. Opening 20A can function as a gas inlet. That is, in the embodiment shown in FIG. 2, gas inlet (lower opening 20A) can be coupled to a gas source coupling device 21A, such as, but not limited to, a swivel conduit, for carrying gas such as air between mask 10A and an external gas source (not shown), such as a blower, or any other suitable device. For example, gas source coupling device 21A may be a generally cylindrical tubular member sized to fit within a distal end, i.e. the end disposed away from the user's face, of faceplate body 17A at faceplate opening 20A.

Gas source coupling device 21A may extend into faceplate body 17A which may also be partially tubular.

Similarly, in the embodiment shown in FIG. 1, lower portion 16 also defines lower opening 20. Lower opening 20 can function as a gas inlet. Gas inlet (lower opening 20) can be coupled to a gas source coupling device 21, such as a swivel conduit, for carrying gas such as air between mask 10 and an external gas source (not shown), such as a blower, or any other suitable device. It is contemplated that the external gas source can encompass, without limitation, any gas delivery or gas generation system capable of supplying gas for consumption by a user. Non-limiting examples of various gas delivery therapies can include but are not limited to continuous positive airway pressure (CPAP) therapy, auto-titration positive airway pressure therapy, and bi-level positive airway pressure (BiPAP) therapy, as noted above. The particular coupling device 21, shown in FIG. 1, or the particular coupling device 21A shown in FIG. 2, is not meant to be limiting and it should be understood that the present invention contemplates a variety of different coupling devices that could be attached, either permanently or selectively, to opening 20, 20A to carry gas to or from mask 10, 10A. Thus, a variety of coupling devices (e.g., with or without swivels on one or both ends, and with or without an exhalation system formed integral to the device) may be substituted for coupling device 21, 21A.

Respiratory interface device 8, and more specifically brace assembly 40, further includes a strap 30, as shown in FIG. 1. Strap 30 may be directly coupled to either mask 10 or brace assembly 40. Strap 30 may be a tension member or an elastic member. Strap 30 may include an adjustment device, such as, but not limited to, a buckle or a hook-and-loop coupling (neither shown). Such an adjustment device is structured to adjust the relative length of strap 30. Strap 30 is sized to extend about the user's head.

Mask 10, 10A also includes a patient contacting cushion 15, 15A. In an exemplary embodiment, shown in FIG. 2, cushion 15A is sealingly coupled to faceplate 12A. Cushion 15A is structured to extend toward the user's face and generally defines the depth of mask 10A. Cushion 15A can be constructed of a wide variety of materials known in the art and can include, but is not limited to, those materials previously described as suitable materials for upper and lower portions 14, 16 and connecting member 18. The particular cushion 15A shown in FIG. 2 is not meant to be limiting and it should be understood that other types of cushion supports or sealing systems that extend between the frame member (e.g., a faceplate 12A shown in FIG. 2) and the user's face, may be substituted for cushion 15A. For example, and without limitation, various cushion configurations can include a double flap cushion, a gel cushion, a gel cushion with a flap, an air-filled cushion, a cushion with a pleat, or multiple cushions (e.g., one inside of the other). Further, it is to be understood that cushion 15A can be detachable and removable from faceplate 12A.

Brace assembly 40, 40A includes a brace body 42, 42A, FIGS. 1 and 2, respectively. The nasal mask exemplary embodiment will be used in the remaining Figures and be referenced in most of the following discussion. It is understood, however, that any description relating to this exemplary embodiment is also applicable to the exemplary embodiment structured to cover the user's nose and mouth discussed above. Brace body 42A is a generally rigid body which may be made from a rigid polymer, such as, but not limited to, polycarbonate, nylon, or polyethylene. Brace body 42A includes a central portion 46A and may have one or more extensions 47A, discussed below. Brace body central portion 46A has an inner side 50A and an outer side 52A. Brace body central portion 46A defines an opening 48A therethrough. Brace body central portion opening 48A is sized to allow gas source coupling device 21A to pass therethrough. Brace body central portion opening 48A is defined by an opening edge 49A.

Brace body extensions 47A are elongated members which may be used for coupling strap(s) 30 to brace assembly 40A. As such, brace body extensions 47A are structured to assist in positioning mask 10A in a proper orientation relative to the user's face. As shown, the most elongated brace body extension 47A extends generally vertically and is structured to contact the user's forehead. It is noted that brace body extension 47A may be arcuate or otherwise curved so as to contact the user's face at selected locations, thereby positioning brace assembly 40A in a selected orientation relative to the user's face.

Mask 10A and brace assembly 40A have at least one mask coupling 60A. Mask coupling 60A is a construct structured to couple mask 10A to brace assembly 40A. Mask coupling 60A, in one exemplary embodiment, is structured to allow mask 10A to move relative to brace assembly 40A along at least one axis, such as a horizontal axis 62A. For example, brace assembly 40 may include horizontally extending pivot pins (not shown) that are structured to be rotatably coupled to mask 10.

In another exemplary embodiment, mask coupling 60A is a floating coupling. That is, mask 10A is coupled to brace assembly 40A but is free to move relative to brace assembly 40. In this embodiment, gas source coupling device 21A passes freely through brace body central portion opening 48A. Other features of gas source coupling device 21A, or mask 10A, such as but not limited to, a bend in gas source coupling device 21A or mask's 10A cross-sectional area being greater than brace body central portion opening 48A cross-sectional area, prevent mask coupling 60A from passing entirely through brace body central portion opening 48A. Thus, both gas source coupling device 21A and therefore mask 10A are coupled to brace body 42A. Mask 10A, however, may both pivot and move in an axial direction relative to brace body 42A. That is, in this configuration, mask 10A may pivot about at least a vertical axis and a horizontal axis relative to brace body 42A as well as move axially relative to brace body 42A.

It is noted that in assembling mask coupling 60A, mask 10A may be placed on brace body inner side 50A and gas source coupling device 21A may be placed on brace body outer side 52A. Gas source coupling device 21A is passed through brace body central portion opening 48A and coupled to faceplate opening 20A. As there are no structures fixedly coupling or directly connecting either gas source coupling device 21A or mask 10A to brace assembly 40A, mask coupling 60A is a floating coupling.

The floating coupling is not structured to orient mask 10A relative to a user's face. That is, a user wears brace assembly 40A which disposed mask 10A in generally the proper location on the user's face, but, if only a floating coupling were used to coupled mask 10A to brace assembly 40A, then use of strap 30, and more specifically tightening of strap 30, would cause brace assembly 40A to directly contact mask 10A and bias mask 10A against a user's face in a random or improper orientation. To prevent such a random orientation a stop made from a rigid material could be used, but this typically creates the same comfort issues as having mask 10A and brace assembly 40A fixed to each other, as discussed above. To provide a comfortable fit and to provide automatic alignment of mask 10A, a flexible membrane assembly 80 disposed between mask 10A and brace assembly 40A. Flexible membrane assembly 80 is structured to provide proper orientation for mask 10A relative to the user's face.

That is, mask coupling 60A includes flexible membrane assembly 80 which provides a soft coupling, or a soft direct coupling, between mask 10A and brace assembly 40A. That is, when flexible membrane assembly 80 is included in mask coupling 60A, mask coupling 60A is a soft coupling. Mask coupling 60A, and more specifically flexible membrane assembly 80, is structured to properly orient mask 10A relative to the user's face. That is, as noted above, brace assembly 40A is structured to contact the user's face at selected locations thereby positioning brace assembly 40A relative to the user's face. Flexible membrane assembly 80 is sized and shaped as needed with respect to brace assembly 40A to position mask 10A in the proper orientation relative to brace assembly 40A and, therefore, the proper orientation relative to the user's face.

Flexible membrane assembly 80 is, in an exemplary embodiment, separate from mask 10A. Flexible membrane assembly 80 is disposed between mask 10A and brace assembly 40A, and more specifically between faceplate outer side 19 and brace assembly inner side 50A. In one exemplary embodiment, flexible membrane assembly 80 includes at least one elongated member, hereinafter a first elongated member 82, made from a resilient material. In an exemplary embodiment, first elongated member 82 is made from silicone, and more specifically liquid silicone rubber, thermoplastic elastomer, foam, rubber, gel (either encased in a membrane/film or not encased). Such a material is generally softer than the material of faceplate 12, 12A. The material of flexible membrane assembly 80, and more specifically of first elongated member 82, may have a Shore A hardness of between about 3 and 80 and may specifically have a Shore A hardness of about 40. First elongated member 82, in an exemplary embodiment, is relatively thin compared to its length and may be described as a "rib." First elongated member 82 has an inner end 84 and an outer end 86. The longitudinal axis of first elongated member 82 extends generally normal to the user's face. That is, for example, if a user is standing in an upright position, the longitudinal axis of first elongated member 82 extends generally horizontally. It is noted that "generally" in this instance is broadly construed in that user facial contours may be very different.

In an exemplary embodiment, shown in FIG. 3, first elongated member 82 is disposed in at least one location about gas source coupling device 21. When gas source coupling device is generally cylindrical, first elongated member 82 is disposed in at least one radial location about gas source coupling device 21. In an exemplary embodiment, mask 10A includes a planar surface 88 that is structured to act as a seat for flexible membrane assembly 80, and more specifically first elongated member 82. Planar surface 88 is disposed generally perpendicular to the longitudinal axis of faceplate body 17A. Alternatively, planar surface 88 may be described as being disposed in a plane generally parallel to the plane of faceplate opening 20A. It is noted that for masks having other shapes, e.g. mask 10, the planar surface structured to be a seat for flexible membrane assembly 80 may have different orientations. Further, first elongated member 82 may be shaped to conform to mask 10A surfaces adjacent to planar surface 88, thereby providing a more secure coupling of first elongated member 82 to mask 10A. That is, for example, the axial surface of elongated member inner end 84 may abut planar surface 88 and a portion of the longitudinal surface of first elongated member 82 may abut a surface of mask 10A.

As shown in FIGS. 3 and 5, first elongated member 82 is disposed at the top of brace assembly mask coupling 60A. Flexible membrane assembly 80, and more specifically first elongated member 82, orients and maintains the position of mask 10A relative to brace assembly 40A as follows. As noted above, the floating coupling between mask 10A and brace assembly 40A would allow mask 10A to move generally freely, i.e. pivot about a horizontal and vertical axes and move axially, relative to brace assembly 40A. With flexible membrane assembly 80, and more specifically first elongated member 82, in place, the minimal spacing between mask 10A and brace assembly 40A is substantially maintained. That is, other than an allowable compression, the degree of which is dependent upon the material used to create first elongated member 82, first elongated member 82 prevents mask 10A from moving toward brace assembly 40A. Thus, the axial movement of mask 10A relative to brace assembly 40A is limited. Further, the rotation of mask 10A about a horizontal axis, as shown, is limited. That is, as mask 10A rotates upwardly, axial surface of elongated member outer end 84 engages brace assembly inner side 50A.

It is noted that, even when first elongated member 82 is mounted on planar surface 88, compression of first elongated member 82 causes first elongated member 82 to be biased toward, and therefore engage, mask 10A and more specifically planar surface 88. Thus, free rotation of mask 10A relative to brace assembly 40A, other than an allowable compression as noted above, is prevented. Thus, the orientation of mask 10A relative to brace assembly 40A is limited by first elongated member 82. Accordingly, by sizing first elongated member 82 based upon mask 10A, brace assembly 40A and the contours of the user's face, the proper orientation of mask 10A may be achieved and substantially maintained. Moreover, the orientation of mask 10A is achieved automatically. That is, the user merely tightens straps 30 and, as brace assembly 40A biases mask 10A towards the user's face, mask 10A will move to the proper orientation without specific adjustment by the user.

Further, it is noted that elongated member 82 may not extend to and contact brace assembly 40A when mask 10A is in all orientations relative to brace assembly 40A. That is, mask 10A moves between at least a first position, wherein mask 10A is not contacting a user's face and is therefore hanging from, and angled downward relative to, brace assembly 40A, and a second position, wherein mask 10A is contacting a user's face and mask planar surface 88 is generally parallel to a vertical plane. In this configuration, elongated member 82 may not extend to and contact brace assembly 40A while in the first position, or even the second position. That is, there may be a gap of between about 0 and 15 mm between first elongated member outer end 86 and brace assembly body inner side (50A). That is, flexible membrane assembly first elongated member 82 is spaced between about 0 and 15 mm from the brace assembly body inner side (50A). In this configuration, mask 10A rotates freely relative to brace assembly 40A until first elongated member outer end 86 contacts brace assembly 40A. Thus, flexible membrane assembly 80 is disposed between, and is structured to engage faceplate outer side 19 and brace assembly inner side 50A. Flexible membrane assembly 80 may, however, be spaced from brace assembly inner side 50A in selected configurations.

Orientation of mask 10A relative to brace assembly 40A may further be enhanced by use of additional elongated members, such as, but not limited to, a second elongated member 90. As shown in FIGS. 4 and 6, flexible membrane assembly 80 includes second elongated member 90, which may also be described as a "rib," having a first end 92 and a second end 94. The axial surface of second elongated member first end 92 may be disposed on, i.e. abut, planar surface 88. As shown, second elongated member 90 is, in an exemplary embodiment, disposed opposite, i.e. 180 degrees about faceplate opening 20A. While not shown in the figures, it is understood that there may be more than one or two elongated members 82, 90 disposed about faceplate opening 20A. Further, the two elongated members 82, 90, as well as any other elongated members, may be disposed in a symmetrical or asymmetrical pattern about faceplate opening 20A.

Similar to flexible membrane assembly first elongated member 82, flexible membrane assembly second elongated member 90 may be spaced between about 0 and 15 mm from the brace assembly body inner side 50A. It is further noted that, while in one exemplary embodiment, flexible membrane assembly 80 is comprised entirely of the same material with the same hardness, and may be a unitary body, in another embodiment, different portions of flexible membrane assembly 80 are comprised of different materials each having different hardness, or, portions of the same material each having different hardness.

In another exemplary embodiment, shown in FIGS. 1 and 7, flexible membrane assembly 80 includes a ring or torus 100 extending about the gas source coupling device 21, 21A. Flexible membrane assembly torus 100 may have a generally constant outer radius (FIG. 1) or be combined with elongated members 82, 90, as shown in FIG. 7, as well as any additional ribs. That is, flexible membrane assembly torus 100 may also be described as having a variable radius. Flexible membrane assembly torus 100 inner radius is generally constant and sized to correspond to the radius of gas source coupling device 21A. The inner, i.e. the side toward the user's face, planar surface of flexible membrane assembly torus 100 may abut mask planar surface 88.

The mask 10A and brace assembly 40A described above may be utilized as follows. A user may position (200) the mask over the user's nose and mouth thereby creating a generally continuous seal between the patient's face and the cushion. Positioning the mask 10A, results in compressing (202) at least a portion of the flexible membrane assembly thereby allowing selective, but limited, movement of the mask relative to the brace assembly. This in turn creates (204) a more complete seal between the patient's face and the cushion.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by on and the same item of hardware. The word "a" or "an" preceding an element does not exclude the presence of a plurality of such elements. In any device claim enumerating several means, several of these means may be embodied by one and the same item of hardware The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A respiratory interface device comprising:
    a mask having a faceplate and a patient contacting cushion, the patient contacting cushion coupled to, and extending about, the faceplate;
    a brace assembly comprising a brace body and at least one mask coupling, wherein the mask and the brace assembly body are coupled at the mask coupling, and wherein the mask coupling is a soft coupling;
    a gas source coupling device;
    the faceplate has an opening therethrough;
    the brace assembly has an opening therethrough, wherein the gas source coupling device extends through the brace assembly opening and into the faceplate opening, thereby coupling the mask and the gas source coupling device, and wherein the gas source coupling device being floatably coupled to the brace assembly at the brace assembly opening by a floating coupling;
    wherein the mask coupling includes a flexible membrane assembly, and wherein the flexible membrane assembly is disposed between the mask and the brace assembly body; and
    the flexible membrane assembly includes a first elongated member disposed in at least one location about the gas source coupling device, the first elongated member having a longitudinal axis that extends generally normal to the user's face.

2. The respiratory interface device of claim 1, wherein the flexible membrane assembly includes a second elongated member disposed at another location about the gas source coupling device and with a longitudinal axis that extends generally normal to the user's face.

3. The respiratory interface device of claim 1, wherein:
    the mask includes a generally planar surface; the flexible membrane assembly first elongated member being disposed between the mask generally planar surface and the brace body;
    the flexible membrane assembly first elongated member having an inner end and an outer end; and
    the flexible membrane assembly first elongated member abutting the mask surface.

4. The respiratory interface device of claim 3, wherein:
    the brace assembly has an inner side;
    the mask pivots between a first position and a second position relative to the brace assembly; and
    when the mask is in the first position, the flexible membrane assembly first elongated member outer end is spaced between about 0.0 and 15.0 mm from the brace assembly inner side.

5. The respiratory interface device of claim 3, wherein:
    the flexible membrane assembly includes a second elongated member disposed at a bottom of the brace assembly mask coupling and with a longitudinal axis that extends generally normal to the user's face;
    the flexible membrane assembly second elongated member being disposed between the mask generally planar surface and the brace body; and
    the flexible membrane assembly second elongated member having an inner end and an outer end.

6. The respiratory interface device of claim 5, wherein:
the mask pivots between a first position and a second position relative to the brace assembly; and
when the mask is in the first position, the flexible membrane assembly second elongated member is spaced between about 0 and 15 mm from the brace assembly body inner surface.

7. The respiratory interface device of claim 5, wherein: the flexible membrane assembly includes a torus, the flexible membrane assembly torus extending about the gas source coupling device.

8. The respiratory interface device of claim 7, wherein: the flexible membrane assembly is made from a material having a Shore A hardness of between about 3 and 80.

9. The respiratory interface device of claim 8, wherein: the flexible membrane assembly is made from a material having a Shore A hardness of about 40.

* * * * *